US00PP12257P2

(12) United States Plant Patent
Lamb et al.

(10) Patent No.: US PP12,257 P2
(45) Date of Patent: Dec. 4, 2001

(54) SPATHIPHYLLUM PLANT NAMED 'AZIZA'

(75) Inventors: Ann E. Lamb, Sebring; David R. Lilly, Boynton Beach; Randy L. Allamand, Lake Placid, all of FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/586,604

(22) Filed: Jun. 2, 2000

(51) Int. Cl.[7] ..... A01H 5/00

(52) U.S. Cl. ..... Plt./364

(58) Field of Search ..... Plt./364

*Primary Examiner*—Bruce R. Campell
*Assistant Examiner*—Kent L. Bell
(74) *Attorney, Agent, or Firm*—Foley & Lardner

(57) ABSTRACT

A new Spathiphyllum plant named 'Aziza' characterized by its large size and its large, elliptic, white spathes which are held just above the foliage. The foliage of 'Aziza' is dark-green, glossy and rigid with a wavy margin. Plants of 'Aziza' are easy to grow and are tolerant of temperature extremes without damage to the foliage.

2 Drawing Sheets

BACKGROUND OF THE INVENTION

The present invention comprises a new and distinct cultivar of Spathiphyllum plant, botanically known as *Spathiphyllum hybrid*, and hereinafter referred to by the cultivar name 'Aziza'.

The new cultivar is the product of a breeding program carried out by the inventors, Ann E. Lamb, David R. Lilly and Randy L. Allamand. The new cultivar named 'Aziza' is the result of a cross made in Apopka, Fla. in November of 1993. The female or seed parent was the cultivar Spathiphyllum 'Lynise' (U.S. Plant Pat. No. 6,145). The male parent was a plant, found among seedling-derived Spathiphyllum 'Mauna Loa', named 'Vibrant' (unpatented) which was selected and maintained by the inventors and used only for breeding purposes.

The new cultivar named 'Aziza' was discovered and selected by the inventors from a group of seedlings of the stated cross in Homestead, Fla. on May 16, 1996. Propagation by tissue culture in the laboratories of Twyford Plant Laboratories, Inc., in Sebring, Fla., under the supervision of the inventors, was used to increase the number of plants for evaluation and has demonstrated the stability of the combination of characteristics as herein described and are firmly fixed and reproduces true to type from generation to generation.

BRIEF DESCRIPTION OF THE INVENTION

The following traits have been repeatedly observed and are determined to be basic characteristics of 'Aziza' which in combination distinguish this Spathiphyllum as a new and distinct cultivar:

1. Plants are large and ideally suited for pot sizes 25 cm or larger;
2. Leaves are dark-green, glossy, rigid and leathery with a wavy margin. The leaf blade is broad and textured;
3. Spathes are white, elliptic, cupped and are held just above the foliage on thick, sturdy peduncles; and
4. Plants are easy to grow and are tolerant of temperature extremes (108° F.–52° F.) without foliar damage.

'Aziza' has not been observed under all possible environmental conditions. The phenotype of the new cultivar may vary significantly with variations in environment such as temperature, light intensity, and daylength, without any change in genotype.

Of the commercial cultivars known to the inventors, the most similar in comparison to 'Aziza' is the parental cultivar 'Lynise'. In comparison to 'Lynise', 'Aziza' has pure white inflorescences while the inflorescences of 'Lynise' are cream-white in color. Plants of 'Aziza' are larger than plants of 'Lynise'. The leaves of 'Aziza' are darker-green, wider, shinier, thicker and more rigid than the leaves of 'Lynise'.

In comparison to the parental cultivar 'Vibrant', plants of 'Aziza' do not grow as large as those of 'Vibrant'. The growth habit of 'Aziza' is more upright and compact than 'Vibrant'. Plants of 'Aziza' are more likely to branch than those of 'Vibrant'. The leaves of 'Aziza' are thicker and very rigid, those of 'Vibrant' are thinner and more flexible. The leaves of 'Aziza' are smaller and narrower than those of 'Vibrant'. The spathes of 'Aziza' are white; the spathes of 'Vibrant' are green and larger than those of 'Aziza'.

BRIEF DESCRIPTION OF THE DRAWING

The accompanying color photographic illustrations show typical characteristics of a 14-month-old plant of 'Aziza' grown in a 25 -cm pot initiated from three microcuttings obtained by tissue culture and grown under appropriate growing conditions, with colors being as nearly true as possible with illustrations of this type.

Sheet 1 is a side view showing the inflorescence and foliage of a plant of 'Aziza'.

Sheet 2 is a close-up view of the inflorescence of the instant plant.

DETAILED BOTANICAL DESCRIPTION

The following observations, measurements and values describe 14 month old plants, finished in 25 cm pots, grown in Homestead, Fla. under greenhouse conditions which closely approximate those generally used in horticultural practice. All color references are measured against The Royal Horticultural Society (R.H.S.) Colour Chart. Colors are approximate as color depends on horticultural practices such as light level and fertilization rate, among others, without, however, any variance in genotype.

Classification:

*Commercial.*—*Spathiphyllum hybrid cv. 'Aziza'.*

Parentage:

*Male parent.*—Selection of Spathiphyllum 'Mauna Loa' named 'Vibrant'.

*Female parent.*—Spathiphyllum 'Lynise'.

Propagation: Vegetative, by tissue culture.

Plant: Under appropriate growing conditions, plant attains a size of approximately 60 cm to 72 cm in height from the soil plane to the tip of the spathe, and approximately 110 cm to 115 cm in width.

Leaves:

*Form.*—The leaf blade is elliptic with a cuneate to obtuse base and an acute apex which curves downward. The margins are entire and distinctly wavy. The midrib is straight over approximately ⅔ the length of the leaf, and curved downward somewhat toward the leaf tip. The leaves are moderately thick, leathery and rigid. The upper leaf surface is textured and glossy.

*Size.*—Leaf blades are approximately 38 cm to 40 cm in length and approximately 16.6 cm to 18.5 cm in width.

*Petiole.*—The petiole is approximately 38 cm to 45 cm in length from the base of the petiole to the base of the leaf blade on primary shoots. Secondary shoots are smaller depending on the age of the shoot. The petiole is approximately 9 mm in diameter at the junction of the geniculum and petiole sheath. The portion of the petiole beneath the geniculum is straight.

*Petiole sheath.*—The petiole sheath is approximately 33 cm to 40 cm in length and approximately 14 mm to 17 mm in width at midpoint. The tip of the petiole sheath is oblique. The petiole sheath terminates at the base of the geniculum.

*Geniculum.*—The geniculum is approximately 5.0 cm to 5.5 cm in length, approximately 1 cm in diameter. The color is greener than, but closest to, RHS 147B.

*Veins.*—Veins are sunken, and the leaf blade convex between veins on the upper surface giving the leaf a textured appearance. The midrib is sunken. Well defined primary veins radiate out from the midrib over the length of the leaf. There are approximately 15 pairs of primary veins on the leaf.

*Color.*—Leaf: Upper surface: Considerably darker than, but closest to, RHS 137A. Lower surface: Darker than, closest to, RHS 147B. Midrib: Upper surface: Darker than, but closest to, RHS 137A. Lower surface: RHS 146C. Petiole: Darker and greener than, but closest to, RHS 137A. Petiole sheath: Darker and greener than, but closest to, RHS 137A.

Inflorescence:

*Immature.*—The spathe is tightly rolled around the spadix and emerges from the petiole sheath. The spathe is fully open approximately when the peduncle is fully elongated — approximately 78 cm to 85 cm above the soil surface, measured at the tallest point. The peduncle is approximately 52 cm to 58 cm in length measured from the crown of the plant to the base of the spathe. It is approximately 7.5 mm to 8 mm in diameter measured at the midpoint of the peduncle. The peduncle is darker and greener than, but closest to, RHS 146B.

*Mature.*—Spathe: Size: The spathe is approximately 26.0 cm to 28.5 cm long and approximately 10.0 cm to 13.5 cm in width. It is cupped, approximately 2.0 cm in depth. Color: Fully open: Adaxial surface: White, RHS 155D, tinged with RHS 148D along the midrib. Abaxial surface: White, RHS 155D. Midrib: Front is RHS 155D tinged with RHS 148D, back is darker and greener than, but closest to RHS 146B. Apex: Front is RHS 155D tinged with RHS 148D, back is RHS 146B. Faded: Adaxial surface: RHS 155D streaked with RHS 146B. Abaxial surface: RHS 155D streaked with RHS 146B. Midrib: Front is RHS 155D streaked with RHS 146B, back is darker than, but closest to, RHS 146B. Apex: Front is RHS 155D streaked with RHS 146B; back is RHS 145B.

*Arrangement.*—The spathe terminates as a straight peduncle which opens vertically above the leaves.

*Shape.*—The spathe is elliptic with a cuneate base and an acute, or slightly cuspidate twisted apex.

*Margin.*—Smooth with occasional undulations, entire.

*Flowering.*—Depending on season, approximately 3 to 4 blossoms will be present on plants. Smaller narrower blossoms may occur on less mature growth.

*Fragrance.*—Sweet, pleasant, moderately fragrant, most noticeable early in the morning.

*Lastingness of individual inflorescence.*—Spathes of 'Aziza' begin to change from pure white streaked with green after about 3–4weeks, becoming almost entirely green after about 6 weeks. Cut inflorescences last about 7 days off the plant.

Reproductive organs:

*Spadix.*—Size: Approximately 13 cm in length and approximately 2.35 cm in diameter. Color: When the spathe unrolls, the spadix is RHS 158B to RHS 158C gradually changing to green, RHS 146C, as the flower fades. Flowers per Spadix: Approximately 275. Stamens: Anthers and filaments are minute and not clearly visible. Pollen: RHS 155D. Pistil: White in color, conical, protruding between the staminate flowers, fixed to the main axil. One pistil per flower. The pistillate flowers extend approximately 3.5 mm beyond the staminate flowers.

Fruit: Oblong to elliptic berry, 7 mm long, 5 mm wide, green RHS 146C tinged with yellow RHS 19B when ripe.

Seeds: Approximately 2 mm in diameter, reniform in shape, light to medium brown in color, surface texture of seed coat is pitted; each individual capsule contains approximately 1–6 seeds, depending on size and degree of pollination, a single inflorescence can yield approximately 825 seeds.

Roots: Thick white roots with fine laterals.

Disease resistance susceptibility: Preventative disease and pest control measures used to grow crops of 'Aziza' are typical of ordinary commercial practice. 'Aziza' has no sensitivity to common pests or pathogens observed to date.

We claim:

1. A new and distinct cultivar of Spathiphyllum plant named 'Aziza', as illustrated and described.

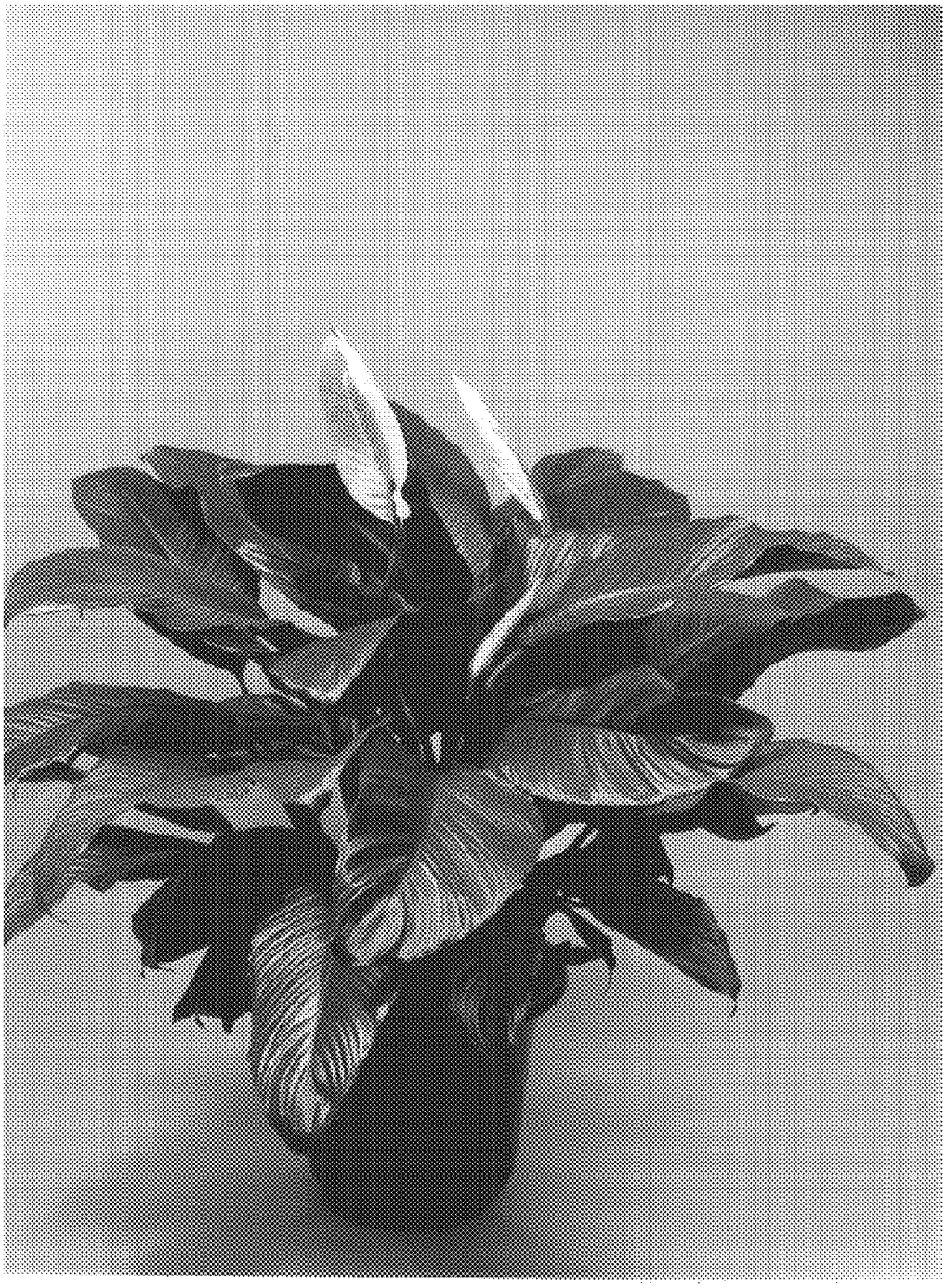

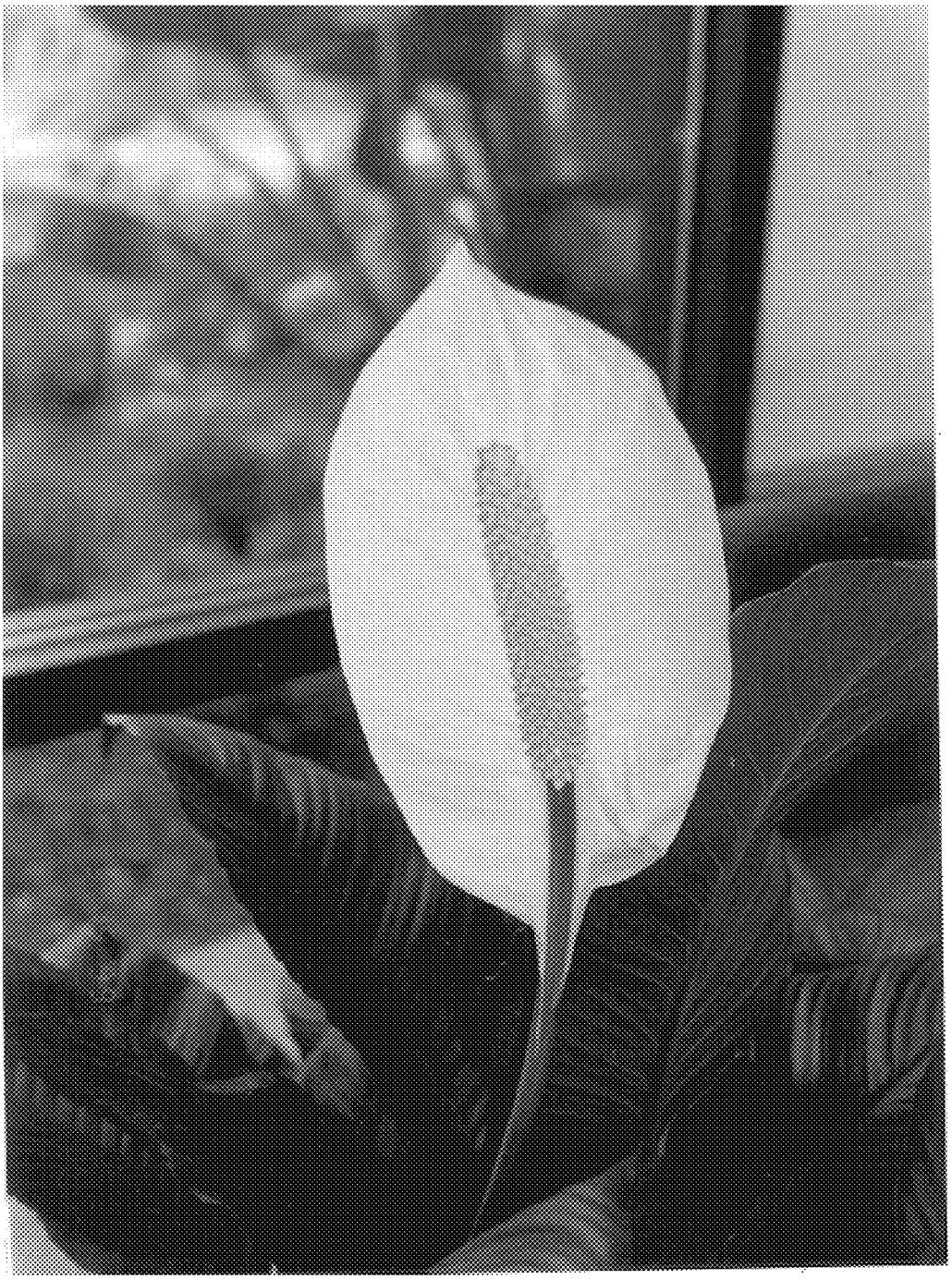

* * * * *